(12) United States Patent
Binnewies et al.

(10) Patent No.: US 7,264,671 B2
(45) Date of Patent: Sep. 4, 2007

(54) SULFUR-MODIFIED ZINC OXIDE

(75) Inventors: Michael Binnewies, Münster (DE);
Sonja Locmelis, Hannover (DE)

(73) Assignee: Universitat Hannover, Hannover (DE)

( * ) Notice: Subject to any disclaimer, the term of this patent is extended or adjusted under 35 U.S.C. 154(b) by 18 days.

(21) Appl. No.: 11/396,900

(22) Filed: Apr. 4, 2006

(65) Prior Publication Data

US 2006/0222605 A1    Oct. 5, 2006

(30) Foreign Application Priority Data

Apr. 5, 2005    (EP)    .................... 05007378

(51) Int. Cl.
*C04B 14/00* (2006.01)
*C09C 1/04* (2006.01)
(52) U.S. Cl. .............. 106/427; 252/301.6 R; 252/301.6 S; 252/588; 424/401; 424/59; 424/641; 502/216; 423/518; 423/566.1; 106/419
(58) Field of Classification Search ........... 106/427, 106/419; 252/301.6 R, 301.6 S, 588; 424/401, 424/59, 641; 502/216; 423/518, 566.1
See application file for complete search history.

(56) References Cited

U.S. PATENT DOCUMENTS 5,750,609 A * 5/1998 Nosu et al. ............. 524/413

6,497,830 B2 * 12/2002 Miyata .................. 252/588
2002/0110695 A1 * 8/2002 Yang et al. ............. 428/447

FOREIGN PATENT DOCUMENTS

GB    WO 2004/108599    * 12/2004
WO    WO 2005/024612    3/2005

OTHER PUBLICATIONS

Meyer et al., Structural properties and bandgap bowling of $Zn_{o1-x}S_x$ thin films deposited by reactive sputtering, Applied Physics Letters, vol. 85, No. 21, Nov. 22, 2004.

* cited by examiner

*Primary Examiner*—J. A. Lorengo
*Assistant Examiner*—Pegah Parvini
(74) *Attorney, Agent, or Firm*—Roylance, Abrams, Berdo & Goodman, L.L.P.

(57) ABSTRACT

The present invention relates to particles or powders of a compound of formula $Zn_{1-y}M_yO_{1-x}S_x$, wherein x has a value in the range from 0.01 to 0.08, M represents a divalent metal and y has a value in the range from 0 to 0.2, the compound having a wurtzite structure.

15 Claims, 1 Drawing Sheet

SULFUR-MODIFIED ZINC OXIDE

FIELD OF THE INVENTION

The present invention relates to a modified zinc oxide in the form of particles or in powder form, that is to say in the form of bulk material. The particles can have a considerable size which may be, or may even exceed, several millimeters.

The invention relates also to articles comprising particles or powders according to the invention, to the use of a particle or powder according to the invention as a UV absorber, and to processes for the preparation of the particles or powders according to the invention.

BACKGROUND OF THE INVENTION

It has long been known to use inorganic oxygen compounds, such as, for example, titanium(IV) oxide and zinc oxide, as absorbers of ultraviolet light, for example in cosmetic sun protection agents or in plastics materials, paints and surface coatings. Zinc oxide is used to a particularly high degree because—unlike titanium(IV) oxide—it does not possess photocatalytic properties.

However, it is disadvantageous that the absorption edge of zinc oxide is at about 380 nm, so that satisfactory absorption in the longer-wave UVA range is not possible.

The primary object of the present invention was, therefore, to provide an inorganic UV absorber which exhibits a high absorption capacity even in the longer-wave UVA range.

SUMMARY OF THE INVENTION

According to the invention, this object is achieved by the provision of particles or powders of a compound of formula $Zn_{1-y}M_yO_{1-x}S_x$ wherein x has a value in the range from 0.01 to 0.08, M represents a divalent metal and y has a value in the range from 0 to 0.2, the compound having a wurtzite structure.

Thin films of a compound of formula $ZnO_{1-x}S_x$ have already been published by B. K. Meyer et al., in Applied Physics Letters, 85, 21, 22 November 2004. However, the mentioned publication does not disclose particles or powders of such a compound as would be required for use on an industrial scale. In addition, Meyer et al. disclose only films having a thickness of approximately 300 nm; there is no indication in the publication that the materials are thermodynamically stable and also obtainable as a bulk material. The same is true of the publication Y.-Z. Yoo, T.-W. Jin, T. Chikow, T. Fukurama, M. Kawasaki, H. Koinuma, Appl. Phys. Lett. 2002, 81, 3798.

Surprisingly, it has now been possible to obtain particles according to the invention in the form of light-greenish, intergrown crystals, the habit of which differs markedly from that of needle-like ZnO crystals. In addition, it has been possible to obtain polycrystalline, light-yellow powders according to the invention.

Particles have a number of advantages over the thin layers known from the prior art: While only extremely small amounts of the order of magnitude of less than 1 microgram are conventionally precipitated with the layers, and the precipitated amount is dependent in principle on the size of the surface onto which precipitation is carried out, particles, and accordingly powders, can be produced in virtually any desired amount using a suitable process (see also hereinbelow in this connection). In addition, it is possible for various applications, using suitable processes (see hereinbelow in this connection), to control the particle size, so that particles—unlike layers—can optimally be adapted to the intended use. The person skilled in the art will not find it too difficult to adjust the particle size as desired by selecting suitable parameters in the preparation processes described hereinbelow. Using the layers known from the prior art it is not possible, for example, to produce suspensions such as are necessary for sun protection agents. Sun protection agents in commercial packs (about 200 ml) currently contain zinc oxide as UV absorber in an order of magnitude of about 1 g.

Furthermore, unlike the layers known from the prior art, the particles according to the invention, even in the form of a pure substance, can readily be stored, packaged, transported and therefore also handled. Accordingly, the particles can be put onto the market, for example as UV absorbers, even without further additions or admixtures, in the form of a raw material/base material for a very wide variety of end products.

BRIEF DESCRIPTION OF THE FIGURE

The ultraviolet and visible light spectral analysis of monocrystals of compounds of formulae ZnO, ZnS and $ZnO_{1-x}S_x$ are shown diagrammatically in the accompanying FIG. 1.

DETAILED DESCRIPTION

Figure 1:
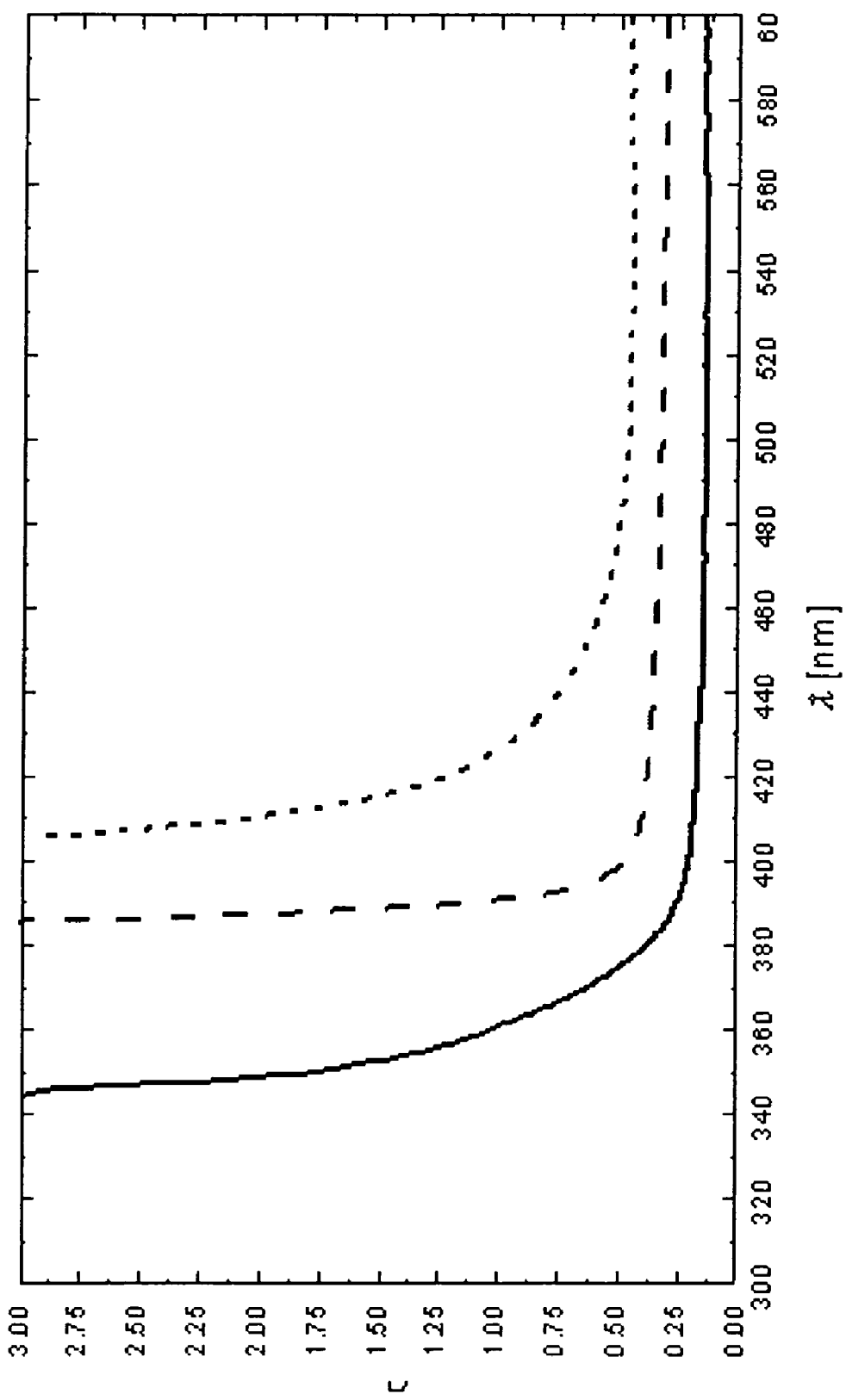

The particles (when referring to individual particulate properties) or powders (when referring to bulk particulate properties) according to the invention of a compound of formula $Zn_{1-y}M_yO_{1-x}S_x$ have an absorption edge that is displaced in comparison with the base compound ZnO. The extent of the displacement of the absorption edge and the modification of the other absorption behavior depend on the amounts of sulfur and divalent metal incorporated into the wurtzite structure. For the compound $ZnO_{0.92}S_{0.08}$, an absorption edge of about 430 nm is obtained, which is accordingly displaced into the longer-wave range compared to the absorption edge of about 380 nm for ZnO. This displacement is particularly surprising because the absorption edge for ZnS is at about 350 nm, and the compound to be used according to the invention accordingly has an absorption edge that does not lie between those of ZnO and ZnS. This finding is confirmed by the numerical values of the band spacing $E_g$: $E_g(ZnO)=3.19$ eV, $E_g(ZnO_{0.95}S_{0.05})=3.01$ eV, $E_g(ZnS)=3.54$ eV. Within the range of from 380 to 430 nm, different absorption edges can be established for compounds of the $ZnO_{1-x}S_x$ type, depending on the chosen value of x.

Particularly convincing results can be achieved with particles or powders according to the invention of a compound of formula $Zn_{1-y}M_yO_{1-x}S_x$ wherein y has the value 0 or a value in the range from 0 to 0.0002. Such particles or powders according to the invention can be prepared using ZnO grades having a correspondingly low degree of contamination, see below in this respect. In particular, but not only, when y has the value 0, that is to say no further divalent metal is incorporated into the compound, x preferably has a value in the range from 0.01 to 0.05. In this range, the compound is thermodynamically stable at 900° C.

The particles or powders according to the invention are advantageously single-phase, but they can also be combined with other particles or powders, e.g. with zinc oxide, to form corresponding mixtures.

Preferred particles and powders according to the invention have a particle size or mean grain size of 300 nm or more. The particle size or mean grain size is preferably in the range from 1 to 10 μm.

In the particles or powders according to the invention, M is preferably selected from the group consisting of: Ti, V, Ca and Sn and is particularly preferably selected from the group consisting of Cr, Mn, Fe, Co, Ni, Cu, Cd and Mg. In order to prepare corresponding particles or powders, there is preferably first prepared a compound of formula $Zn_{1-y}M_yO$, which is subsequently converted into the compound of formula $Zn_{1-y}M_yO_{1-x}S_x$. With regard to the preparation of compounds of formula $Zn_{1-y}M_yO$, reference is made to the following publications: S. Locmelis, R. Wartchow, G. Patzke, M. Binnewies; *Z. Anorg. Allg. Chem.* 1999, 625, 661; S. Locmelis, M. Binnewies; *Z. Anorg. Allg. Chem.* 1999, 625, 1573; S. Locmelis, M. Binnewies; *Z. Anorg. Allg. Chem.* 1999, 625, 1578; G. Patzke, S. Locmelis, R. Wartchow, M. Binnewies; *J. Cryst. Growth* 1999, 203, 141; K. Ullrich, S. Locmelis, M. Binnewies, K. D. Becker; *Phase Transitions,* 2003, 76, 103; S. Locmelis, Dissertation of the University of Hanover 1999; B. K. Meyer, A. Polity, B. Farangis, Y. He, D. Hasselkamp, Th. Krämer, C. Wang, *Appl. Phys. Lett.* 2004, 85, 4929. The person skilled in the art will determine, by means of a small number of preliminary tests that are within the existing level of routine skill, whether there are any restrictions, and where appropriate what restrictions there are, as regards the quantities of metal M and sulfur that can be incorporated into the wurtzite structure. The maximum values for x and y given above are not desirable and/or achievable for every metal M.

The invention relates also to articles comprising particles or powder according to the invention. Preferably, articles according to the invention comprise the particles or powder in the region of their surface, so that the particles or powder are able to develop a UV-absorbing action when the article in question is used.

Preferred articles according to the invention are cosmetic preparations (in particular sun protection formulations), plastics materials, paints and surface coatings. Each of the mentioned articles preferably comprises particles or powders according to the invention in an amount such that a UV-absorbing action occurs.

The present invention accordingly relates also to the use of a particle or powder according to the invention as a UV absorber.

The particles or powders according to the invention—like the base compound zinc oxide—have medically and pharmaceutically valuable properties. The invention accordingly relates also to articles (in particular pharmaceutical preparations) which comprise particles according to the invention or powders according to the invention in an antimicrobially effective amount and/or in an amount that promotes the healing of wounds. The particles/powders according to the invention can also be incorporated in outstanding manner into preparations against zinc-deficiency diseases, for example against: Acrodermatitis enteropathica (a hereditary skin disease), cirrhosis of the liver, sickle cell anaemia, diabetes, rheumatic arthritis, arteriosclerosis, ulcerated legs. Such preparations are preferably intended for internal use. Zinc preparations comprising the particles/powders according to the invention can also be used in: burns, wounds, various skin diseases, and infections. The formulation of a preparation according to the invention generally corresponds to the formulation of corresponding pharmaceutical preparations based on zinc oxide.

The invention relates also to a process for the preparation of the particles or powders according to the invention. The process according to the invention comprises the step of heating ZnO and ZnS together, preferably in the presence of a halogen or halogen compound.

An alternative process according to the invention for the preparation of the particles or powders according to the invention comprises the following steps:
a. producing an aqueous suspension of zinc hydroxide,
b. contacting the zinc hydroxide with sulfide ions so that a reaction precipitate forms, and
c. subjecting the reaction precipitate to heat, preferably a temperature that is sufficiently high to temper the precipitate.

In the two alternative processes according to the invention, the steps of "heating together" or "subjecting to heat" bring about a solids reaction which ultimately yields the particles or powders according to the invention.

The described preparation processes according to the invention differ from the processes known from the prior art for the production of UV-absorbing films comprising the composition $ZnO_{(1-x)}S_x$ in that the solids reaction takes place in a fluid thermodynamic equilibrium. Moreover, in preferred preparation processes according to the invention for particles according to the invention, an intermediate is frequently of crucial importance: For example, where ZnO and ZnS are heated in the presence of bromine, ZnBr forms such an intermediate. For precipitation from suspensions it is additionally of crucial importance to control the sulfide ion concentration.

The invention relates also to the use of the particles or powders according to the invention as pigments. Particles/powders according to the invention having a content of Mn atoms in the range $0.001<y<0.2$ are particularly valuable pigment particles or powders, because the incorporation of manganese atoms results in an intense wine-red color.

Finally, the invention relates also to a method of absorbing UV radiation comprising the following step: irradiating a particle or powder according to the invention with UV radiation.

EXAMPLES

Further preferred embodiments of the present invention will become apparent from the accompanying patent claims and the following examples.

Example 1

Preparation of a Powder of a Compound of Formula $ZnO_{1-x}S_x$ (x≦0.05)

Mixtures having the following compositions were prepared in separate investigations:

21.78 mmol. ZnO/0.22 mmol. ZnS
21.56 mmol. ZnO/0.44 mmol. ZnS
21.34 mmol. ZnO/0.66 mmol. ZnS
21.12 mmol. ZnO/0.88 mmol. ZnS
20.90 mmol. ZnO/1.10 mmol. ZnS The grain sizes of the starting solids materials used were in each case in the range from 1 to 10 μm.

Each mixture accordingly comprises a total of 22 mol. of Zn. The mathematical value of x varied from 0.01 to 0.05.

The mixtures were each transferred to quartz-glass containers; the containers were evacuated and then filled with a small amount of bromine, closed and maintained at a temperature of 950° C. for at least 5 days. Single-phase, light-yellow powders of a compound of formula $ZnO_{1-x}S_x$ were formed, the particles of the powder formed having a grain size in the range from 1 to 10 μm.

Note: In additional tests it was found that, with a mathematical value of x of over 0.05, a second phase having a high sulfur content was formed in addition to the $ZnO_{1-x}S_x$ phase.

Example 2

Preparation of Crystals (Large Crystalline Particles) of a Compound of Formula $ZnO_{1-x}S_x$ by Precipitation from the Gas Phase Mixtures of ZnO and ZnS were prepared, for example a mixture consisting of 1701 mg (20.9 mmol.) of zinc oxide and 107 mg (1.1 mmol.) of zinc sulfide.

In a quartz-glass ampoule (inside diameter 10 mm; length 190 mm) in a horizontal two-zone oven, the mixtures were exposed to a temperature gradient of, for example, 1000° C.→900° C. A small amount of bromine (or alternatively a corresponding amount of a different halogen or of a halogen compound) was added as transport agent; the bromine pressure (starting pressure) was 0.5 bar. A plurality of light-greenish, intergrown $ZnO_{1-x}S_x$ crystals having a size of several millimetres were obtained.

The lattice parameters of the $ZnO_{1-x}S_x$ phases were determined by means of X-rays; they differ only slightly from those of pure ZnO: a=325.251(17) pm, c=520.906(6) pm, V=47.742(4)·$10^6$ $pm^3$. ZnO (for comparison): a=325.156(5) pm, c=520.906(6) pm, V=47.6951(14)·$10^6$ $pm^3$.

Example 3

Preparation of a Powder of a Compound of Formula $ZnO_{1-x}S_x$ by Precipitation from Solution First step: Sodium hydroxide was added to an aqueous zinc salt solution, for example a saturated $ZnSO_4$ solution, so that zinc hydroxide was obtained as precipitate. The zinc hydroxide was filtered off.

Second step: The precipitate was washed with distilled water until neutral.

Third step: The washed precipitate was suspended in water, and $H_2S$ gas was passed into the resulting suspension for 15 minutes. Alternatively, in different forms of the process, an aqueous $H_2S$ solution or another preparation that supplies sulfide ions was added.

The resulting precipitate was filtered off and then subjected to heat, preferably first for 12 hours at 500° C. and then for a further 12 hours at 800° C. The product was a light-yellow powder of a compound of formula $ZnO_{1-x}S_x$.

Analytical Methods

In our own investigations, the following analytical methods were used to determine the composition, to confirm the single-phase nature of products according to the invention and to determine the grain size distribution:

Methods for Determining the Composition:
a. Energy-dispersive X-ray spectroscopy (EDX) (EDAX, SUTW detector, Röntgenanalytik Messtechnik GmbH. ProgrammVision 32).
b. Wavelength-dispersive X-ray spectroscopy: WDX. (Cameca)

Method for Determining the Single-phase Nature:
X-ray powder diffractometry (Stadi P with PSD, Stoe, Darmstadt, Cu—$K_\alpha$ radiation, 40 kV, 30 mA. Evaluation software: WinXPow, Stoe).

Method for Determining the Grain Size Distribution:
a. Scanning electron microscospy: SEM (FEI-Philips, XL 30, W cathode).
b. Dynamic light scattering (Zetasizer Nano Series, Malvern Instruments Ltd. 2003)

Example 4

UV/Vis Spectra of Monocrystals of Compounds of Formulae ZnO, ZnS and $ZnO_{1-x}S_x$ UV/Vis is spectra of monocrystals of compounds of formulae ZnO, ZnS and $ZnO_{1-x}S_x$ were recorded and are shown diagrammatically in the accompanying FIG. 1. The abbreviations used in FIG. 1 have the following meanings:
λ [nm]: wavelength
A: absorbance: A=log($I_0$/I), wherein $I_0$ and I are the intensity of the incident and transmitted light
solid line: graph for ZnS
broken line: graph for ZnO
dotted line: graph for $ZnO_{1-x}S_x$ (x=0.05)

In FIG. 1, a y-displacement of 0.5 unit was carried out for ZnO (broken line) and a y-displacement of 0.3 unit was carried out for $ZnO_{1-x}S_x$ (dotted line).

The invention claimed is:

1. Particle or powder of a compound of formula $Zn_{1-y}M_yO_{1-x}S_x$, wherein:
   x has a value in the range from 0.01 to 0.08,
   M represents a divalent metal,
   y has a value in the range from 0 to 0.2, and the compound has a wurtzite structure.

2. Particle or powder according to claim 1, wherein y has a value in the range from 0 to 0.0002.

3. Particle or powder according to claim 1, wherein x has a value in the range from 0.01 to 0.05.

4. Particle or powder according to claim 1, wherein the particle or powder is single-phase.

5. Particle or powder according to claim 1, wherein the particle has a particle size or the powder has a mean grain size of 300 nm or more.

6. Particle or powder according to claim 5, wherein the particle has a particle size or the powder has a mean grain size in the range from 1 to 500 μm.

7. Particle or powder according to claim 1, wherein M is selected from the group consisting of: Cr, Mn, Fe, Co, Ni, Cu, Cd and Mg.

8. Article comprising particles or powder according to claim 1.

9. Article according to claim 8, wherein the article comprises the particles or powder in the region of its surface, so that the particles or powder are able to develop a UV-absorbing action when the article is used.

10. Article according to claim 9, wherein the article is a cosmetic or pharmaceutical preparation, a plastics material, a paint or a surface coating.

11. Article according to claim 8, wherein the article comprises said particles or powder in an antimicrobially effective amount and/or in an amount that promotes the healing of wounds.

12. An ultraviolet light absorbent composition comprising a particle or powder according to claim 1.

13. Process for the preparation of powders according to claim 1, comprising the following step:
   heating ZnO and ZnS together in the presence of a halogen or halogen compound.

14. Process for the preparation of powders according to claim 13, comprising the following steps:
  producing an aqueous suspension of zinc hydroxide,
  contacting the zinc hydroxide with sulfide anions so that a reaction precipitate forms, and
  subjecting the reaction precipitate to heat.

15. Method of absorbing UV radiation, comprising the following step:
  exposing a particle or powder according to claim 1 to UV radiation.

* * * * *

UNITED STATES PATENT AND TRADEMARK OFFICE
CERTIFICATE OF CORRECTION

PATENT NO.        : 7,264,671 B2                                      Page 1 of 1
APPLICATION NO. : 11/396900
DATED             : September 4, 2007
INVENTOR(S)       : Michael Binnewies et al.

It is certified that error appears in the above-identified patent and that said Letters Patent is hereby corrected as shown below:

TITLE PAGE:

Under Section (56) References Cited:

At Col 2, under Other Publications change "bowling" to --bowing--

Signed and Sealed this

Eighteenth Day of December, 2007

JON W. DUDAS
*Director of the United States Patent and Trademark Office*